United States Patent [19]

Cutrer

[11] Patent Number: 5,647,374
[45] Date of Patent: Jul. 15, 1997

[54] NEEDLE FOR IMAGING AND SAMPLING

[75] Inventor: L. Michael Cutrer, Chatsworth, Calif.

[73] Assignee: North American Scientific, North Hollywood, Calif.

[21] Appl. No.: 366,494

[22] Filed: Dec. 30, 1994

[51] Int. Cl.⁶ ................................................. A61B 10/00
[52] U.S. Cl. .......................... 128/749; 604/165; 128/654
[58] Field of Search .............................. 128/749–757, 128/662.02, 657, 654; 604/164, 165

[56] References Cited

U.S. PATENT DOCUMENTS

| | | | |
|---|---|---|---|
| 4,781,198 | 11/1988 | Kanabrocki | 128/654 |
| 5,081,997 | 1/1992 | Bosley, Jr. et al. | 128/754 |
| 5,158,084 | 10/1992 | Ghiatas | 128/657 |
| 5,224,488 | 7/1993 | Neuffer | 128/751 |
| 5,257,632 | 11/1993 | Turkel et al. | 128/754 |
| 5,490,521 | 2/1996 | Davis et al. | 128/662.02 |

*Primary Examiner*—Max Hindenburg
*Assistant Examiner*—Pamela L. Wingood
*Attorney, Agent, or Firm*—Loeb & Loeb

[57] ABSTRACT

An instrument and method for the biopsy of tumors, such as breast lesions, are disclosed. A stylus comprises a tube having radioactive material in the tip capable of being imaged, the stylus contained within a needle. An image of the tip of the needle can be traced as it penetrates a human body, is guided toward an imaged tissue mass, and is placed within the tumor.

18 Claims, 3 Drawing Sheets

NEEDLE FOR IMAGING AND SAMPLING

BRIEF DESCRIPTION OF THE INVENTION

1. Field of the Invention

The present invention relates to an instrument and method useful in the biopsy of non-palpable tumors and more particularly to a needle containing a sealed stylus containing a radioactive element capable of being imaged on a nuclear medicine scintillation imaging system.

2. Description of the Relevant Art

The early detection of cancer is essential to the treatment and recovery of the patient. Typically cancerous tissues, such as breast lesions, have been initially identified through self examination and/or mammography. Often, small tumors cannot be identified for several reasons such as presence of scar tissue, tissue density, etc. Therefore, detection requires the disease to have reached a more advanced level. For identified lesions, the tissue is then biopsied.

The biopsy procedure utilizes a needle of appropriate length and diameter and an associated stylus. The needle consists of a hollow stainless steel tube having a sharp distal end to allow for penetration of tissue and a proximate end. On the proximate end, a hub, which is typically a formed plastic unit, is fixed to the needle, and is adapted for attachment to a syringe. During many medical procedures, it is necessary for the needle to be inserted into a patient. In certain situations, it is necessary for the needle to be fitted with a mating stylus. A stylus usually consists of a solid length of stainless steel having a distal and proximate end. At the proximate end, the stylus has fixed a hub adapted to mate with the needle's hub typically through a detent and a prong. The stylus slides into the needle aligning its distal end with the sharpened end of the needle and with the hubs of the needle and stylus engaging. The stylus then is virtually completely housed within the needle and acts as a plug, blocking material from entering the needle during insertion. Once the needle is properly inserted and positioned, the stylus is withdrawn and a syringe may be attached to the needle and cellular material removed (cytology) or in other cases a guide wire inserted through the needle and into the area of interest.

During a breast biopsy of non palpable lesions for example, a location wire is be placed into the breast tumor prior to surgical removal. This is done by inserting the distal end of a needle housing an associated stylus into the tumor. The stylus is removed and a wire with a small spring hooked end is slid down the needle into the tumor where it is fixed into the tissue of interest. The needle can then be removed leaving the wire as a guide directly to the tumor for the surgeon.

To identify non-palpable tumors, a technology has been developed using an FDA approved radiopharmaceutical imaging agent. That technology has been presented at the 1994 meeting of the Radiological Society of North America meeting held in Chicago, Ill. on Nov., 28, 1994. Researchers have found a new indicator for diagnosis of certain cancerous tissues. An affinity by at least some cancerous tissues results in the uptake of the radiopharmaceutical imaging agent provides an image on a nuclear medicine scintillation imaging system. An instrument has been developed for a "Stereotaxic Localization Device" at Harbor-UCLA Medical Center which allows accurate determination of the exact three dimensional position of the imaged cancerous tissue. A presentation describing details of this stereotaxic localization device has been presented at the 1994 Society of Nuclear Medicine Meeting in June 1994 at Orlando, Fla.

Research has shown that through the use of radiopharmaceutical and the stereotaxic localization, the presence of certain types of previously undetectable lesions can be identified. Research also indicates that although extremely small tumors can now be imaged, and their position accurately identified, placement of a needle and guide wire into the imaged tissue would be difficult. A device that allows for precise location and placement of a needle and a guide wire into a small imaged tissue mass is desirable.

It is an object of an embodiment of the present invention to more readily permit biopsies of cancerous tissue. It is a second object of an embodiment of this invention to permit such biopsies with reduced patient discomfort. It is a third object of an embodiment of this invention to permit the accurate placement of a needle. It is a fourth object to permit accurate placement of a surgical guide wire into the tumor when necessary.

SUMMARY OF THE PREFERRED EMBODIMENTS

These and other objectives are met with an embodiment of the present invention. An embodiment comprises a needle and novel stylus assembly. The stylus is sealed and has radioactive material in the distal tip capable of being imaged. The stylus is designed to be placed within a needle, aligning the distal end of the stylus with the hole in the sharpened end of the needle. The needle with the stylus can penetrate the tissue and be guided while the radioactive tip is imaged in three dimensions and directed toward the previously imaged tissue mass through the visualized image of the radioactive region within the distal end of the stylus. With the physician observing the imaged stylus tip, the needle can be directed so that it enters the tissue mass.

Once the needle has entered the tissue mass, the stylus can be removed from the needle and a hooked guide wire can be slid down the needle and accurately placed into a very small lesion or a syringe attached for cytological sampling.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION OF THE PREFERRED EMBODIMENTS

The following is a description of the preferred embodiments of the present invention.

Figure 1:
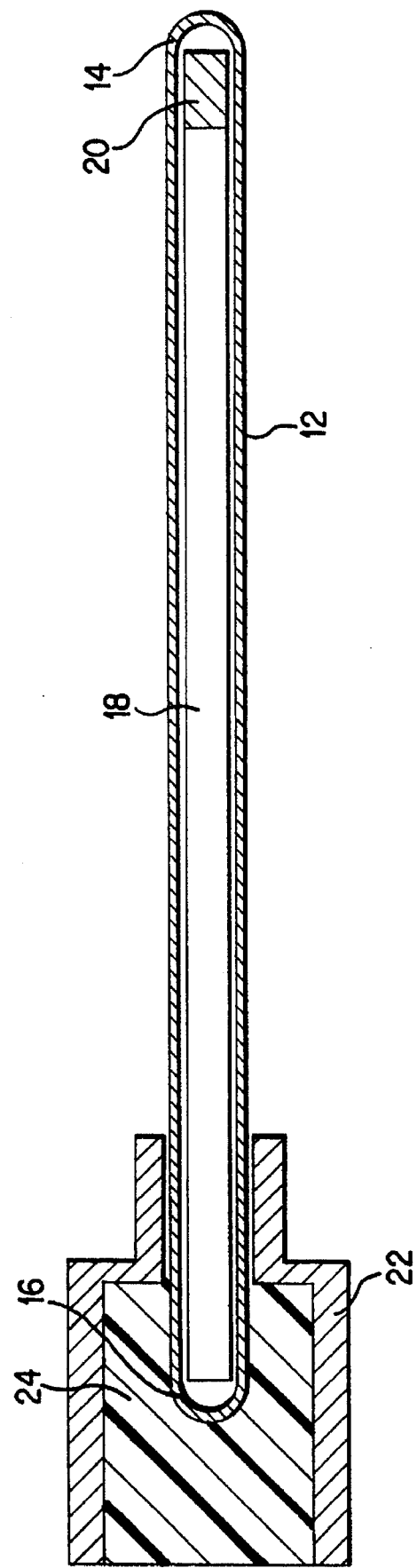
FIG. 1 is a sectional view of a stylus in accordance with an embodiment of the present invention.

As depicted in FIG. 1, an embodiment 10 of the present invention is a stylus useful in the biopsy of certain tissues such as breast lesions. The body 12 of the embodiment 10 is a hollow cylindrical tube 12 having a distal end 14 and a proximate end 16. The distal end 14 of the tube is hermetically sealed. A wire 18 is positioned within the hollow cylindrical tube 12 with a radioactive material 20 such as Cobalt-57 disposed about the end of the wire 18 located at the distal end 14 of the tube.

The hollow cylindrical body 12 of the stylus 10 is a material compatible with contact with the human body and for the containment of a small amount of radioactive material. Preferably the tube is medical grade stainless steel.

At least the distal end 14 of the tube 12 is sealed. It may be desirable to seal both ends of the tube 14 and 16. A method of sealing the ends of the tube 14 and 16 is welding. Other means of sealing the tube include, but are not limited to plugging, crimping, or gluing.

In the embodiment 10 of the present invention, a wire 18 is contained within the tube 12. The wire 18 is a material of sufficient rigidity to allow for the insertion and placement of the end of the wire 18 against the sealed, distal end of the tube 14 and capable of receiving an amount of radioactive material 20 thereon. Nickel is the preferred material for the wire.

The radioactive material 20 deposited on the wire is a suitable radioisotope, and preferably is a gammer emitter such as Cobalt-57. The radioactive material 20 may be deposited about the end of the stylus tube 14 in the form of an ion exchange resin, absorption on nylon, cellulose, or the like, absorption and fusion in a ceramic matrix, evaporated salt, solution or electro-deposition and overplating of the metal surface, with electro-deposition being the most preferred.

In the embodiment 10, a hub 22 is attached to the proximate end of the tube 16. The hub 22 may have a male member for securing the stylus 10 to a detent on a mating hub of a needle (not shown). In one embodiment the hub 22 is made of aluminum and is attached to the tube by means of a high temperature epoxy 24, capable of withstanding the heat requirements of sterilization. Alternatively, the hub 22 and tube 12 can both be made of stainless steel, in a unitary welded assembly, thereby eliminating the need for an epoxy.

Figure 2:
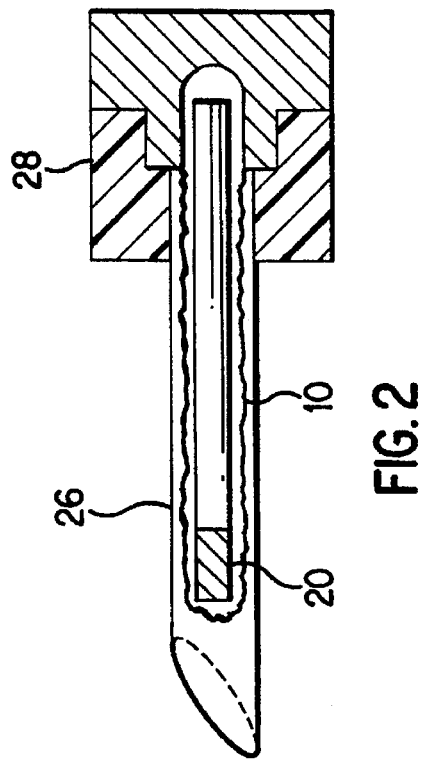
FIG. 2 shows a sectional view of the stylus housed within a needle.

FIG. 2 depicts the embodiment 10 housed within a needle 26. The distal end of the stylus 10 containing the radioactive material 20 is substantially aligned with a hole formed near the sharpened end of the needle 26. The needle 26 is preferably medical grade stainless steel.

The needle 26 has a hub 28 attached to the proximate end of the needle. The hub 28 is typically a formed plastic unit with a detent 23 for engaging the a male member 25 of hub 22 of the stylus. When the stylus 10 is removed from within the needle 26, the hub of the needle can be used to attach and engage an opening of a syringe.

Figure 3:
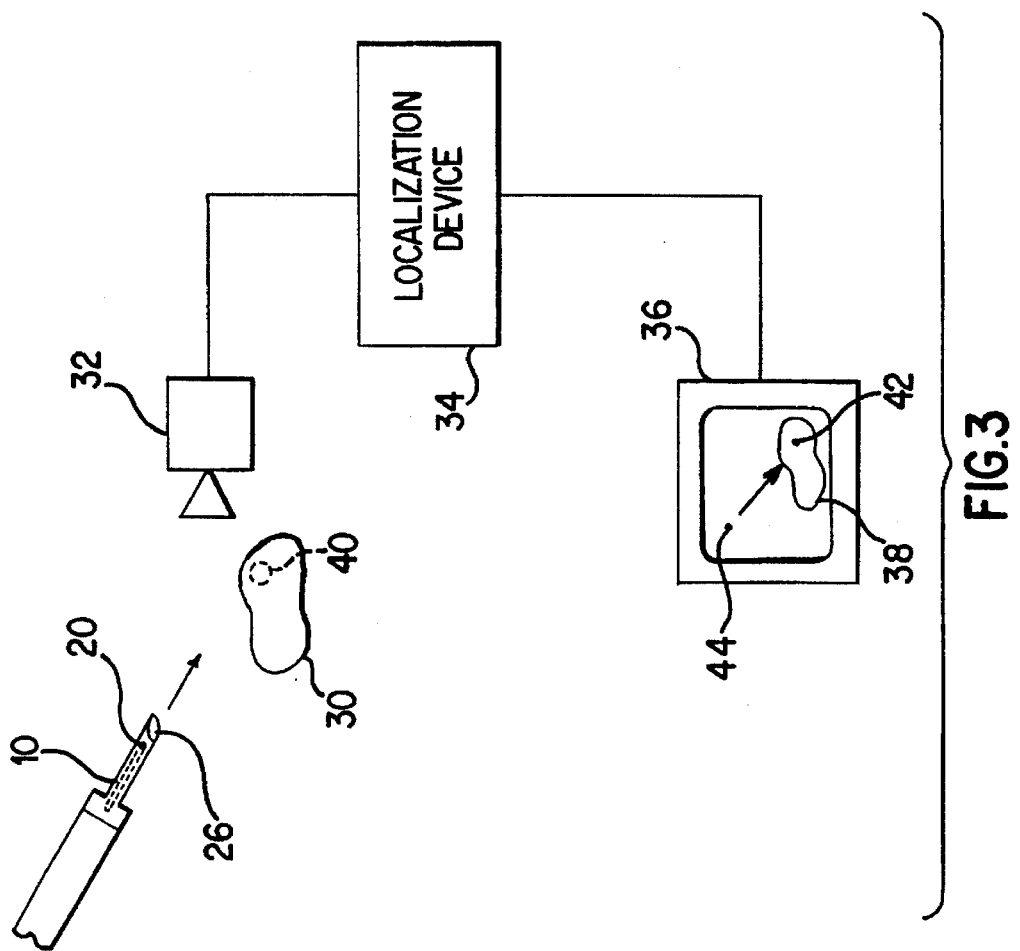
FIG. 3 illustrates placement of a needle with a stylus into a tumor using an embodiment of the invention.

The method of using a stylus and needle assembly to locate an imaged cancerous tissue mass is described in connection with FIG. 3. First, a radiologist images an area of the human body 30 by having the patient injected with a radiopharmaceutical imaging agent so that the lesions can be imaged. A scintillation system sends information to a monitor 36 on which an image 38 of the tissue 30 can be viewed. If a suspected mass 40 appears as an image 42 on the monitor 36, the needle 26 housing the mated stylus 10 with the radioactive material 20 located within the tip of the needle 26 is inserted while viewing the image 42 of the tissue 40 of interest. The imaged tip of the needle can then be guided toward the imaged tissue mass by visually observing the images of the needle tip 44 and the tumor 40 on the monitor 36 with the stereotaxic localization device (not shown) discussed above or otherwise. The needle 26 can then be accurately inserted in a small tumor 40 that would otherwise be very difficult to locate. Finally, the stylus 10 is removed from the needle 26.

Once the stylus 10 is removed, in a first embodiment, the accurate location of the cancerous tissue mass is followed by sliding a spring hooked guide wire down through the needle. The hooked guide wire is then inserted into the tumor. Then the needle can be removed, leaving a guide wire for the surgeon to locate and remove the tumor. Alternatively, a syringe (not shown) can be attached to the hub of the needle, permitting removal of cellular matter from the tissue mass for purposes of cytological studies.

Figure 4:
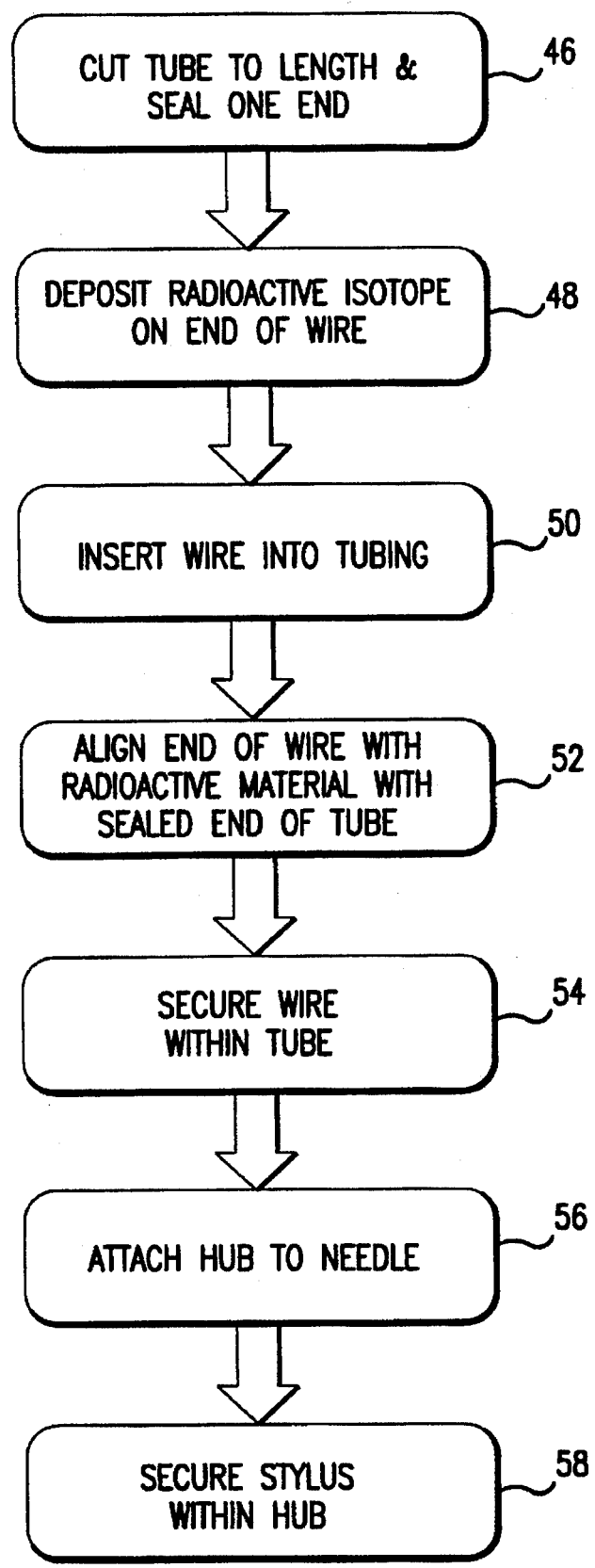
FIG. 4 depicts the steps of manufacturing the stylus and needle assembly.

FIG. 4 depicts the steps of manufacturing the stylus and needle assembly. The manufacture of the stylus begins with the sealing of one end of a length of tubing 46. Radioactive material is deposited, through electro-deposition or otherwise, on the end of the wire 48. The end of the wire with the radioactive material is inserted into the tubing 50. The radioactive material on the wire is aligned with the sealed end of the tube 52. Finally, the wire is secured within the tube 54.

Another embodiment of the invention is the manufacture of the stylus as described above with two additional steps. The wire at the open end of the tube is cut to the length of the tube. The open end of the tube is then sealed. As described above, sealing the end of the tube can be achieved through any of a number of means.

Alternatively, the stylus can be made from a solid rod of an inactive metal. A portion of the distal end such as a length of one centimeter or less is electroplated with a suitable radioactive isotope such as Cobalt 57. The radioactive length is then sealed beneath an overplating of inactive material such as nickel. The size of the radioactive region may vary depending upon application and sensitivity of imaging systems.

In one embodiment of the invention, a stylus was formed by cutting number 27 gauge tube having an 0.016" exterior diameter and an inner diameter of 0.008" to the appropriate length to plug the entire length of the bore of a number 22 gauge needle when fitted with a hub to mate in a housed position with the needle. A 0.005" wire of appropriate length was electroplated with 50 micro curies of Cobalt 57 over a one centimeter length at the distal end and then the wire was inserted into the tube so that the plated end was located within the distal end of the tubing. Both ends of the tube were then sealed by welding and a hub was secured to the proximate end. The stylus was then inserted into a number 22 gauge needle to be later positioned in tissue while observing the stylus with a single photon emission computerized tomography and the stereotaxic location device described above.

Further, the dimensions for the area or the volume of the metal within the stylus that is radioactive will depend upon the nature of the image that is desired on imaging device. Points, lines, triangles or other shapes on the display of the imaging device may be readily obtained by controlling the area that is plated for example. Further, the amount of radioactive material that is used depends upon the sensitivity of the particular imaging equipment being used and is readily adjustable in the manufacturing process for different imaging equipment as is known by those of skill in the art.

A further embodiment of the present invention involves the method of placing the stylus within a needle 56 and securing the stylus within the needle 58 with a locking means. The locking means can include the engaging hubs described above or any other means of securing the stylus within the needle, including snaps, threaded grooves, mated couplings, and the like.

It should be noted that an embodiment of the invention useful in biopsy and other cytology procedures is shown in the drawings for purposes of illustration only. However, it will be recognized that further embodiments of the invention may be used in other areas where nuclear medicine and imaging are used for diagnosis and/or treatment.

What is claimed is:

1. A device comprising:
   a hollow cylindrical needle having a distal end and a proximate end, said distal end being sharpened;
   a stylus comprising:
      a hollow cylindrical tube having a distal end and a proximate end, at least the distal end of the tube being sealed; and
      a point source radioactive material disposed within the distal end of the tube;
   said stylus located within the needle, the distal end of the stylus being in substantial alignment with the distal end of the needle; and
   means for securing the stylus within said needle.

2. The method of using a needle having a sharpened distal end and a proximate end, a hollow stylus located within the needle, a radioactive material contained within one end of the stylus capable of being imaged, the end of the stylus containing the radioactive material being in substantial alignment with the sharpened end of the needle, the method comprising the steps of:
   imaging a cancerous tissue mass in a human body through the uptake of a radiopharmaceutical agent;
   inserting the needle into the human body;
   guiding the imaged radioactive end of the stylus within the needle toward the imaged tissue mass;
   inserting the sharpened end of the needle into the tissue mass; and
   withdrawing the stylus from the inside of the needle.

3. The method of using a device in claim 2 further comprising the step of:
   withdrawing matter from the tissue mass.

4. The method of using a device of claim 2 further comprising the steps of:
   sliding a hooked guide wire through the needle;
   inserting the hooked guide wire into the tissue mass; and
   removing the needle.

5. The device of claim 1 wherein the securing means further comprises:
   a hub having a male member attached to the proximate end of the tube; and
   a hub having a detent attached to the proximate end of the needle, said male member engaged with the detent.

6. The device of claim 5 wherein the hub is attached to the proximate end of the tube by an epoxy.

7. The device of claim 5 wherein the hub is aluminum.

8. The device of claim 5 wherein the hub is stainless steel.

9. The device of claim 8 wherein the hub is welded to the proximate end of the tube.

10. A device comprising:
    a hollow cylindrical needle having a distal and proximate end;
    a stylus comprising:
       a hollow cylindrical tube having a distal end and proximate end,
       a stylus having a distal and proximate end, the stylus housing a point source radioactive material disposed sealed within the distal end of the stylus, and the stylus being secured at least partially within the needle such that the radioactive material is located adjacent to the distal end of the needle.

11. The device of claim 2, wherein the needle is stainless steel.

12. The device of claim 10, wherein the needle is stainless steel.

13. The device of claim 10, wherein the stylus is detachably secured to the needle by a hub.

14. The device of claim 13, wherein the hub has a male portion and a female portion, the male portion being attached to either of the proximate end of the needle and the stylus and the female portion being attached to the proximate end of the other of the stylus and the needle.

15. The device of claim 1, wherein the radioactive substance is cobalt 57.

16. The device of claim 10, wherein the radioactive substance is cobalt 57.

17. The device of claim 15, wherein the cobalt 57 is plated on a wire housed within the stylus.

18. The device of claim 16, wherein the cobalt 57 is plated on a wire housed within the stylus.

* * * * *